United States Patent [19]

Toussaint et al.

[11] 4,229,346

[45] Oct. 21, 1980

[54] PRODUCTION OF HEXAMETHYLENIMINE

[75] Inventors: Herbert Toussaint, Frankenthal; Klaus Adelsberger, Neckargemuend; Herwig Hoffmann, Frankenthal, all of Fed. Rep. of Germany

[73] Assignee: BASF Aktiengesellschaft, Fed. Rep. of Germany

[21] Appl. No.: 556,469

[22] Filed: Mar. 7, 1975

[30] Foreign Application Priority Data

Mar. 28, 1974 [DE] Fed. Rep. of Germany ....... 2414930

[51] Int. Cl.$^3$ .......................................... C07D 295/02
[52] U.S. Cl. ............................................. 260/239 B
[58] Field of Search ..................................... 260/239 B

[56] References Cited

FOREIGN PATENT DOCUMENTS 920606 2/1973 Canada ................................ 260/239 B
51-63184 6/1976 Japan .................................. 260/239 B

OTHER PUBLICATIONS

Yasumura, Chem. Abs., 59, 2813c, (1963).
Nagaoka et al., Chem. Abs., 75, 125130d, (1971).

Primary Examiner—Mark L. Berch
Attorney, Agent, or Firm—Keil & Witherspoon

[57] ABSTRACT

Hexamethylenimine (azocycloheptane) is produced from hexamethylenediamine by elimination of ammonia in a high-boiling solvent at a low concentration of hexamethyleneimine.

12 Claims, 1 Drawing Figure

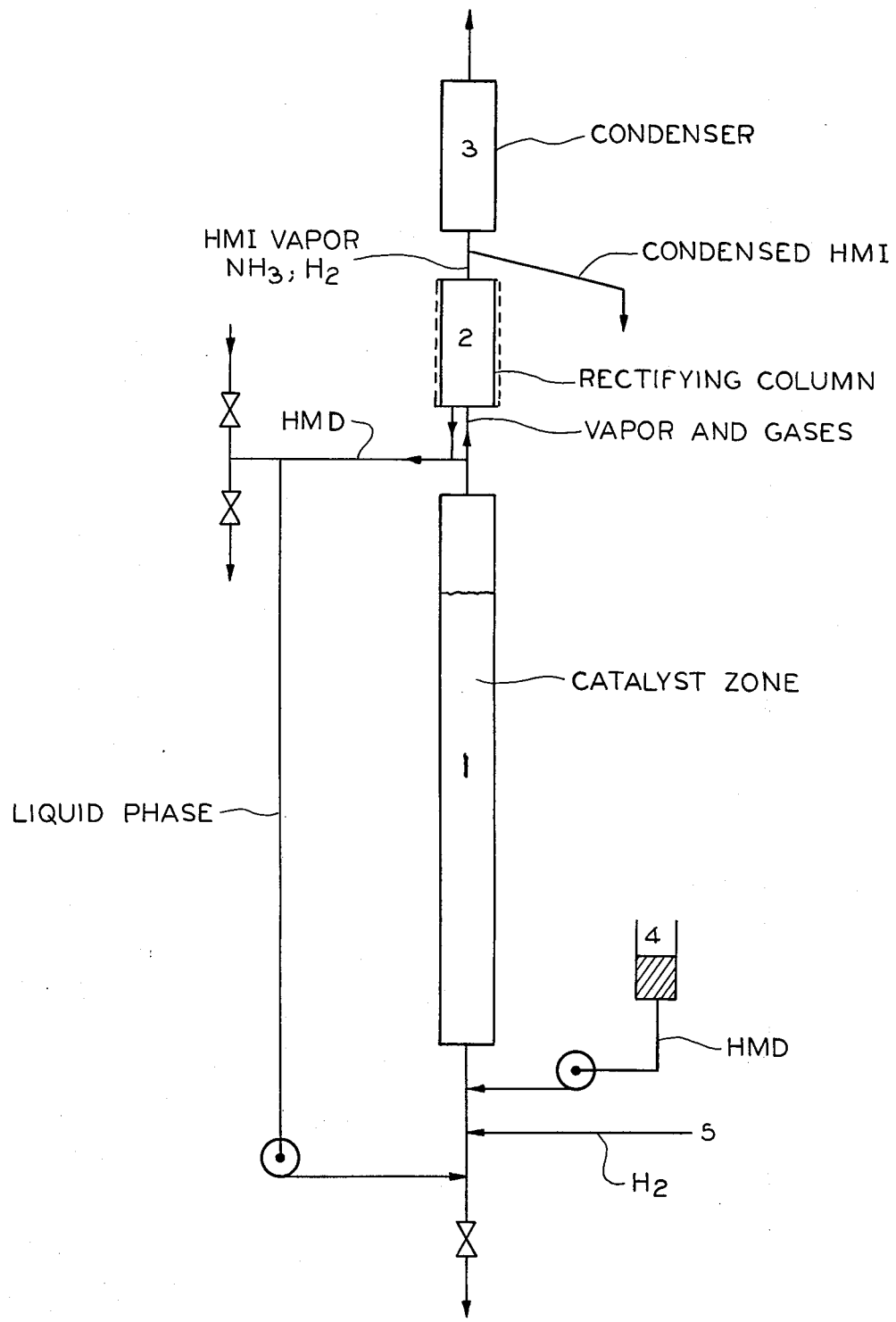

PRODUCTION OF HEXAMETHYLENIMINE

The invention relates to a special continuous process for producing hexamethylenimine (HMI) by elimination of ammonia with ring closure from hexamethylenediamine (HMD) and/or its technical oligomers in the presence of hydrogen and a hydrogenation catalyst and in the liquid phase.

It is known to obtain HMI from HMD. For instance, German Pat. No. 738,448 teaches the reaction in the gas phase in contact with an alumina catalyst, there being, however, no hydrogen present.

For the same reaction in the liquid phase U.S. Pat. No. 3,652,545 (col. 4, 11. 58 ff.) gives a yield of only 50%. Furthermore, pressures of more than 200 bars are stated to be necessary. This patent also deals, inter alia, with the production of HMI from hexanediol, which method also has several serious drawbacks.

Processes for the production of HMD in which HMI is obtained as a byproduct are also well known in the art. However, the yields are unsatisfactory and can only be improved by using high temperatures or expensive reducing agents.

The ring closure reaction mentioned above has recently been attempted by analogy to the manufacture of pyrrolidine and piperidine (Kindler and Matthies, Ber., 96, (1963) pp. 924–929, especially pp. 924 ff.)

Unfortunately, HMD tends, under the conditions discussed by Kindler et al, to form polymers, sometimes with the elimination of ammonia, instead of closing to form the HMI ring. However, only small amounts of HMI are formed in these prior art processes.

Mention may be made here of other routes to HMD, for instance starting from acrolein (U.S. Pat. No. 3,635,951), ε-caprolactam (U.S. Pat. No. 2,181,140), bis-(6-amino-N-hexyl)-amine (German Pat. No. 1,138,780) and ε-caprolactone (British Pat. No. 1,185,310).

We have now found that the abovementioned process gives excellent yields when the reaction is carried out in a chemically inert high boiling solvent having a boiling point (at atmospheric pressure) of at least 140° C., when the HMD concentration in the reaction mixture does not exceed 250 g/l, and when the HMI formed is continuously distilled off.

It goes without saying that, during distillation, HMD is advantageously held back, which in the apparatus shown in the drawing is easy to achieve by placing a short fractionating column on the reaction vessel and, if necessary, refluxing a certain amount of HMI.

A particular advantage of this process over gas phase processes is that no dehydrohexamethylenimine isomers can be detected in the HMI obtained. These isomers are difficult to separate from HMI by distillation.

The reaction temperature depends on the type of hydrogenation catalyst employed and the operating pressure; with conventional cobalt catalysts (supported or unsupported), e.g., modified with nickel, manganese, copper, chromium, etc., it is generally from 140° to 250° C., assuming a pressure of from atmospheric to about 10 bars. Under these conditions, HMI boils off at the reaction temperature as it is formed (the boiling temperature of HMI at atmospheric pressure is approx. 139° C.; the boiling point of HMD is about 205° C.).

When other catalysts, such as Raney nickel and precious metal catalysts, and supported or unsupported catalysts of another type, are used, the most favorable reaction temperature may be set up if desired by employing slight sub- or superatmospheric pressure; suitable pressures are from 0.3 to 3 bars absolute. It is, however, preferred and in most cases advantageous to operate at substantially atmospheric pressure.

Suitable hydrogenation catalysts for the process of the invention are supported or unsupported catalysts. Effective catalysts are those for instance which contain, as catalytically active components, at least one of the metals nickel, cobalt, iron, manganese, silver, copper and chromium. Precious metals, for example palladium, may also be contained in the catalyst. Examples of carriers are aluminum oxide, silicates and silicic acid.

A catalyst which has proved to be particularly suitable contains, on a carrier, 5 to 25% of nickel, 0.5 to 10% of copper, and 0.1 to 5% of manganese. It is also favorable to add small amounts of phosphoric acid, for instance 0.1 to 5%. A particularly suitable carrier in this case is silica gel.

A special feature of the process is that it can be carried out at atmospheric pressure. However, this feature is not intended to limit the invention as the process can with appropriate equipment, be operated within a range of from 0.1 to 50 bars, especially 0.7 to 20 bars. The maximum operating temperature depends inevitably on the pressure if rapid escape of the HMD supplied is to be prevented. A temperature range of from 120° to 280° C. is suitable, and especially from 180° to 225° C. On occasion, a fairly high temperature has a favorable influence particularly on the use of the distillation residue obtained in the production of HMD, which residue generally contains oligomers of HMD.

The process of the invention may be carried out within a broad but relatively low concentration range, approximately from 10 to 250 g of HMD per liter of liquid phase. To a certain extent the yield is observed to improve as the HMD concentration drops; for economical reasons, a concentration of about 3 to 10%, based on the reaction mixture, is preferred.

Hydrogen does not enter into the stoichiometric equation of the reaction of HMD to give HMI, but is, like the hydrogenation catalyst, necessary. To expel the ammonia which forms from the reaction mixture an inert gas would be sufficient, but we have found that it is necessary to add hydrogen at least in admixture and, preferably, to use just hydrogen. It has proved to be particularly economical to recycle the hydrogen gas after separation of the entrained HMI and ammonia.

Suitable inert high-boiling solvents are particularly polynuclear and preferably polynuclear aromatic hydrocarbons which are resistant to hydrogenation at atmospheric pressure and which are suitable as heat transfer liquids, for instance diphenyl ether, diphenylmethane and its derivatives, triaryldimethanes and Decalin, and mixtures thereof. Broadly speaking, the solvents mentioned have molecular weights of from 120 to about 600; they may be selected, e.g., from the group comprising $C_{10}$ to $C_{30}$ aromatic, cycloaliphatic and araliphatic hydrocarbons having 2 to 4 rings in the molecule; $C_{10}$ to $C_{30}$ polyalkylene polyamines; $C_{10}$ to $C_{30}$ polyalkylene polyglycols and ethers thereof, the term "polyalkylene" being understood to comprise $C_2$ to $C_8$ polymethane chain elements; esters and amides of polycarboxylic acids, said amides if desired being N-alkylated; esters, phenolic esters and amides of inorganic mono- or polybasic acids, said amides if desired being N-alkylated. Polymethylene polyamines which are often present during the reaction and whose structure has generally not been investigated may be present even in fairly high concentrations and do not as a rule cause any trouble. It may be advisable to replace some of the solvent by fresh solvent (either continuously or discontinuously) to keep the enrichment of byproducts in reasonable limits.

Solvent requirements are low as experience shows that the total volume increases slowly due to the formation of relatively high molecular weight amines, so that there is no need to add further solvent. If suitable high molecular weight amines are available which fulfil the abovementioned conditions a solvent of different chemical nature is not necessary even for the first charge; the solvent according to the invention may therefore be exclusively a high-boiling amine.

A solvent may in isolated cases form an azeotrope with HMI, but this has no effect on the operability of the process of the invention. A suitable apparatus (see Drawing) consists of a vertical tube (1) charged with the hydrogenation catalyst and through which the circulating liquid phase, HMD (4) and hydrogen (5) are continuously passed upwardly. In the upper portion of the reactor there remains a space free from catalyst so that gases and vapors on the one hand and the liquid phase on the other can separate. The liquid phase is passed to the lower end of the reactor and pumped through it again. Gases and vapors are passed to an insulated rectifying column (2) of suitable dimensions and which is operated in such a manner that HMD which has also been evaporated can be withdrawn at the bottom and introduced into the liquid phase cycle and that HMI vapor, ammonia and hydrogen pass from the top end of the column into a condenser (3), where highly concentrated HMI is condensed. By regulating the removal from the liquid phase cycle, the liquid level in the upper portion of the reactor is kept almost constant.

Advantageously, the reactor is operated in such a manner that 5 to 100 liters of hydrogen flows through it per hour per $cm^2$ of tube cross-section. However, these limits are not critical as the way the layers are arranged in the catalyst bed and the design of the equipment also have an influence.

The rate at which the liquid phase is pumped through the reactor influences of course the average residence time of the HMD. Suitable residence times are from 2 to 20 minutes. The most suitable value is best determined from case to case and depends on the reaction temperature and the apparatus.

Another, more simple arrangement which in many cases is sufficient for fairly small amounts consists of a heatable stirred vessel partially filled with solvent and which possesses means for feeding in fresh HMD and a device for distilling off the HMI. In this apparatus it is advantageous to use a dispersed catalyst, e.g., Raney nickel.

EXAMPLE 1

A vertical heatable reaction tube having a capacity of 930 parts by volume is charged with 850 parts by volume of a catalyst containing 16% by weight of nickel, 5% by weight of copper, 1% by weight of manganese and 1% by weight of $P_2O_5$ on silica gel. The apparatus is filled with a high-boiling heat exchange liquid (Marlotherm S ®) (according the the manufacturers a mixture of isomeric triaryldimethanes) to such an extent that after heating to 205° to 208° C. the liquid phase can be recycled. 200,000 parts by volume of hydrogen and 72 parts by volume of HMD are supplied per hour to the bottom end of the tube. The liquid phase is pumped in such a manner that the circulation time is about 9 minutes. Distillation gives 59 parts by volume of HMI per hour having a purity of 95% (yield: 94% of theory).

EXAMPLE 2

A round-bottomed flask having a capacity of 1,000 parts by volume and equipped with a stirrer, gas feed line, thermometer, reservoir and superposed packed column having a capacity of 1,200 parts by volume is charged with 200 parts by volume of hexa-n-butyl-phosphoric acid triamide and 24 parts of Raney nickel. The flask is heated to 198° to 204° C., 210,000 parts by volume of hydrogen is passed in per hour, and 482 parts by volume of HMD is dripped in evenly over a period of 7 hours. Distillation gives 311 parts by volume of HMI having a purity of 82% (yield: 66% of theory).

We claim:

1. A process for the continuous manufacture of hexamethylenimine which comprises passing hydrogen and a liquid phase of hexamethylene diamine in an inert liquid solvent through a reaction zone in contact with a hydrogenation catalyst containing, as catalytically active compounds, at least one of the metals selected from the group consisting of nickel, cobalt, iron, manganese, silver, copper and chromium and maintained at 120° to 280° C. and 0.1 to 50 bars pressure, said inert solvent having a boiling point at atmospheric pressure of at least 140° C. and the concentration of said hexamethylene diamine in the reaction mixture being about 3 to 10% and continuously distilling off hexamethylenimine from said reaction zone.

2. A process as set forth in claim 1 wherein said pressure is atmospheric to about 10 bars and said temperature is 140° to 250°.

3. A process is set forth in claim 1 wherein said pressure is 0.3 to 3 bars absolute.

4. A process as set forth in claim 1 wherein said pressure is 0.7 to 20 bars and said temperature is 180° to 225° C.

5. A process as set forth in claim 1 wherein reaction zone is tubular and said hydrogen is passed through said reaction zone at a rate of 5 to 100 liters per hour per $cm^2$ of the tubular cross section.

6. A process as set forth in claim 1 wherein reaction zone is tubular and said hydrogen is passed through said reaction zone at a rate of 5 to 100 liters per hour per $cm^2$ of the tubular cross section and said pressure is atmospheric pressure.

7. A process as set forth in claim 1 wherein said pressure is atmospheric pressure and said temperature is 140° to 250° C.

8. A process as set forth in claim 1 wherein the distilled hexamethylene imine vapor contains vapors of hexamethylene diamine, and the latter vapors are separated from the hexamethylene imine vapors by condensation, the condensate being recycled to the reaction zone.

9. A process for the continuous manufacture of hexamethylenimine which comprises passing hydrogen and a liquid phase of hexamethylene diamine in an inert liquid solvent continuously through a reaction zone in contact with a hydrogenation catalyst consisting essentially of 5 to 25% of nickel, 0.5 to 10% of copper and 0.1 to 5% of manganese supported on a catalyst carrier and maintained at 120° to 280° C. and 0.1 to 50 bars pressure, said inert solvent having a boiling point at atmospheric pressure of at least 140° C. and the concentration of said hexamethylene diamine in the liquid phase being about 10 to 250 grams per liter of liquid phase, continuously distilling off hexamethylenimine from said reaction zone, and recycling at least a portion of the liquid phase which is withdrawn from said reaction zone back to the feed end of said reaction zone with fresh hexamethylene diamine being added to the recycled liquid phase.

10. A process for the continuous manufacture of hexamethylenimine which comprises passing hydrogen and a liquid phase of hexamethylene diamine in an inert liquid solvent continuously through a reaction zone in contact with a hydrogenation catalyst containing, as catalytically active components, at least one of the metals selected from the group consisting of nickel, cobalt, iron, manganese, silver, copper and chromium and maintained at 120° to 280° C. and 0.1 to 50 bars pressure, said inert solvent having a boiling point at atmospheric pressure of at least 140° C. and the concentration of said hexamethylene diamine in the liquid phase being about 3 to 10% by weight per liter of liquid phase, continuously distilling off hexamethylenimine from said reaction zone, and recycling at least a portion of the liquid phase which is withdrawn from said reaction zone back to the feed end of said reaction zone with fresh hexamethylene diamine being added to the recycled liquid phase.

11. A process for the continuous manufacture of hexamethylenimine which comprises passing hydrogen and a liquid phase of hexamethylene diamine in an inert liquid solvent through a reaction zone in contact with a hydrogenation catalyst consisting essentially of 5–25% nickel, 0.5 to 10% of copper and 0.1 to 5% of manganese supported on a catalyst carrier and maintained at 120° to 280° C. and 0.1 to 50 bars pressure, said inert solvent having a boiling point at atmospheric pressure of at least 140° C. and the concentration of said hexamethylene diamine in the liquid phase being about 10 to 250 grams per liter of liquid phase, and continuously distilling off hexamethylenimine from said reaction zone.

12. A process for the continuous manufacture of hexamethylenimine which comprises the steps of passing hydrogen and a liquid phase of hexamethylenediamine in an inert liquid solvent through a reaction zone maintained at 120° C. to 280° C. and 0.1 to 50 bars pressure in contact with a hydrogenation catalyst containing, as catalytically active components, at least one of the metals selected from the group consisting of nickel, cobalt, iron, manganese, silver, copper and chromium, the concentration of said hexamethylene diamine in the reaction mixture being about 3 to 10% and continuously distilling off hexamethylenimine from said reaction zone, said inert solvent having a boiling point at atmospheric pressure of at least 140° C.

* * * * *

UNITED STATES PATENT AND TRADEMARK OFFICE
CERTIFICATE OF CORRECTION

PATENT NO. : 4,229,346
DATED : October 21, 1980
INVENTOR(S) : HERBERT TOUSSAINT, KLAUS ADELSBERGER and HERWIG HOFFMANN It is certified that error appears in the above—identified patent and that said Letters Patent is hereby corrected as shown below:

On Column 4, claim 1, line 25: "compounds" should be changed to --components--.

On Column 4, claim 3, line 37: "is" should read --as--.

Signed and Sealed this

Tenth Day of March 1981

[SEAL]

Attest:

RENE D. TEGTMEYER

Attesting Officer

Acting Commissioner of Patents and Trademarks